(12) United States Patent
Yang

(10) Patent No.: US 10,898,279 B2
(45) Date of Patent: Jan. 26, 2021

(54) MEDICAL SYSTEMS, DEVICES, AND RELATED METHODS

(71) Applicant: Boston Scientific Scimed, Inc., Maple Grove, MN (US)

(72) Inventor: Jiandong Yang, Pleasanton, CA (US)

(73) Assignee: Boston Scientific Scimed, Inc., Maple Grove, MN (US)

(*) Notice: Subject to any disclaimer, the term of this patent is extended or adjusted under 35 U.S.C. 154(b) by 208 days.

(21) Appl. No.: 16/151,692

(22) Filed: Oct. 4, 2018

(65) Prior Publication Data

US 2019/0110845 A1    Apr. 18, 2019

Related U.S. Application Data

(60) Provisional application No. 62/572,205, filed on Oct. 13, 2017.

(51) Int. Cl.
*A61B 34/00* (2016.01)
*A61B 18/20* (2006.01)
(Continued)

(52) U.S. Cl.
CPC .............. *A61B 34/25* (2016.02); *A61B 18/20* (2013.01); *A61B 18/24* (2013.01); *A61B 2017/00017* (2013.01); *A61B 2017/00199* (2013.01); *A61B 2017/00212* (2013.01); *A61B 2017/00973* (2013.01); *A61B 2018/0094* (2013.01);
(Continued)

(58) Field of Classification Search
CPC ......... A61B 34/25; A61B 18/20; A61B 18/24; A61B 2017/00212; A61B 2017/00017; A61B 2017/00199; A61B 2018/00708; A61B 2018/0094; A61B 2018/00958;
(Continued)

(56) References Cited

U.S. PATENT DOCUMENTS 3,785,238 A * 1/1974 Wheeler ................... G10D 1/08
84/312 P
4,266,626 A * 5/1981 Shuler .................... B62D 11/04
180/6.48
(Continued)

FOREIGN PATENT DOCUMENTS

WO    WO 2007/005507         1/2007

OTHER PUBLICATIONS

"Surgical Guide," GreenLightHPS High Performance System, AMS Solutions for Life, 2007, 8 pages.
(Continued)

*Primary Examiner* — Catherine M Voorhees
(74) *Attorney, Agent, or Firm* — Bookoff McAndrews, PLLC

(57) ABSTRACT

A method of controlling a laser source to deliver laser energy through a medical device includes adjusting a laser source parameter including at least one of a laser power, a laser energy, a frequency, and a pulse width of the laser source. The laser source parameters are adjustable through a first action or series of actions on a foot pedal assembly operably coupled to a laser control unit. The method also includes activating the laser source. The activation of the laser source includes a second action or series of actions on the foot pedal assembly, and the second series of actions is different from the first action or actions.

20 Claims, 6 Drawing Sheets

(51) Int. Cl.
*A61B 17/00* (2006.01)
*A61B 18/24* (2006.01)
*A61B 18/00* (2006.01)

(52) U.S. Cl.
CPC .............. *A61B 2018/00708* (2013.01); *A61B 2018/00958* (2013.01); *A61B 2018/00982* (2013.01)

(58) Field of Classification Search
CPC . A61B 2018/00982; A61B 2017/00973; A61F 9/008
See application file for complete search history.

(56) References Cited

U.S. PATENT DOCUMENTS

| | | | | |
|---|---|---|---|---|
| 4,590,598 A | * | 5/1986 | O'Harra, II | H01S 3/104 372/25 |
| 2007/0053640 A1 | * | 3/2007 | Goell | A61F 9/008 385/123 |
| 2009/0105698 A1 | * | 4/2009 | Hodel | A61B 18/22 606/11 |
| 2010/0198200 A1 | * | 8/2010 | Horvath | A61B 17/00 606/10 |
| 2015/0148615 A1 | * | 5/2015 | Brennan | A61B 50/33 600/249 |
| 2016/0074110 A1 | * | 3/2016 | Hezit-Yamit | A61B 18/1492 606/41 |
| 2017/0189108 A1 | * | 7/2017 | Melsky | A61B 18/082 |

OTHER PUBLICATIONS http://www.lumenis.com/Solutions/Surgical/Holmium-Laser-Training.
http://www.lumenis.com/Solutions/Surgical/lumenis-pulse-120H.
http://www.drsantoshagrawal.com/laser-surgeries-prostate-kidney-stone.html.
International Preliminary Report on Patentability and Written Opinion issued in International Application No. PCT/US2018/054337, dated Feb. 11, 2019 (13 pages).

* cited by examiner

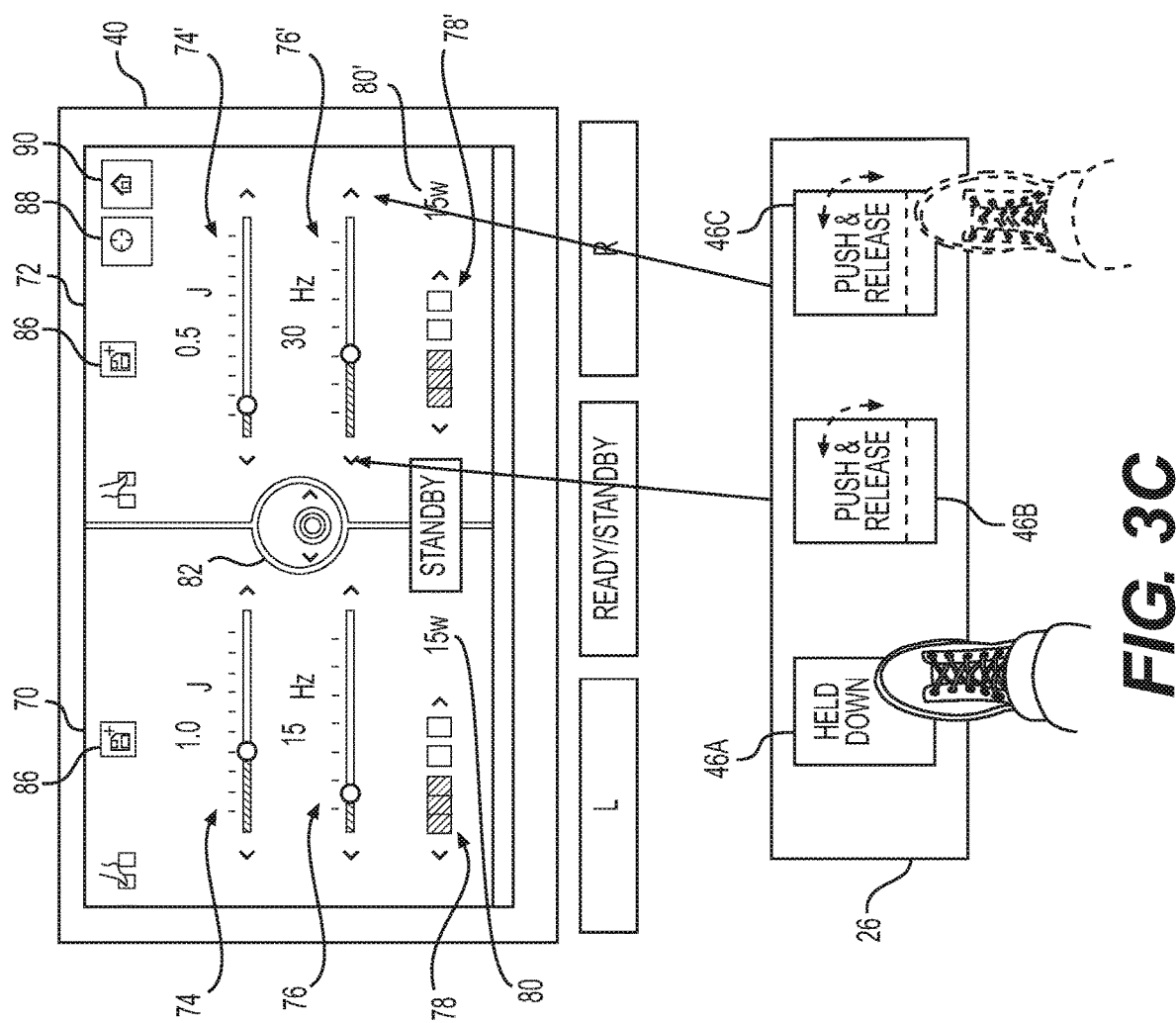

MEDICAL SYSTEMS, DEVICES, AND RELATED METHODS

CROSS-REFERENCE TO RELATED APPLICATIONS

This patent application claims the benefit of priority under 35 U.S.C. § 119 to U.S. Provisional Patent Application No. 62/572,205, filed Oct. 13, 2017, which is herein incorporated by reference in its entirety.

TECHNICAL FIELD

Various aspects of the present disclosure relate generally to systems, devices, and methods useful in medical procedures. More specifically, the present disclosure relates to systems, devices, and methods for adjusting and activating medical devices in medical procedures.

BACKGROUND

Laser energy is used in a wide variety of medical procedures, including urology, neurology, otorhinolaryngology, ophthalmology, gastroenterology, cardiology, and gynecology. Various procedures, and even different portions of the same procedure, often require different levels and intensities of laser energy, which are delivered to cauterize, ablate, break-up, or otherwise treat tissue or other material in a patient. Generally, a user may control and/or modify the settings for the laser energy by inputting or adjusting the settings on a hand-based control module through buttons, dials, or a touch screen. However, in a surgical setting, the user usually is holding at least one medical device in his or her hands and may not be within arm's reach of the control module, which may increase the time and/or the number of medical professionals required during the procedure. Moreover, touching components on the control module while also performing the procedure introduces sterilization and cleanliness issues, as well as increasing the chances of user error, further complicating and prolonging the procedure and exposing the patient to greater risk.

The systems, devices, and methods of the current disclosure may rectify some of the deficiencies described above, and/or address other aspects of the prior art.

SUMMARY

Examples of the present disclosure relate to, among other things, medical systems, devices, and methods. Each of the examples disclosed herein may include one or more of the features described in connection with any of the other disclosed examples.

In one aspect, this disclosure includes a method of controlling a laser source to deliver laser energy through a medical device. The method may include adjusting a laser source parameter including at least one of a laser power, a laser energy, a frequency, and a pulse width of the laser source, wherein the laser source parameters are adjustable through a first action or series of actions on a foot pedal assembly operably coupled to a laser control unit, and activating the laser source, wherein the activation of the laser source includes a second action or series of actions on the foot pedal assembly, and wherein the second series of actions is different from the first action or actions.

The method may further include one or more of the following features. The method may further include positioning the medical device by deflecting a distal end of a delivery shaft via action on a deflection lever on a handle of the medical device. The step of adjusting the laser source parameter may include an action on the foot pedal assembly to enter a laser settings mode. The foot pedal assembly may include a plurality of foot actuators. The foot pedal assembly may include at least a first foot actuator, a second foot actuator, and a third foot actuator.

The first action or series of actions on the foot pedal assembly may include simultaneous depression of at least two foot actuators to enter the laser settings mode. The first action or series of actions on the foot pedal assembly to enter a setting mode may include depression of only one foot actuator for a period of time. The first action or series of actions on the foot pedal assembly may include an action on the foot pedal assembly to toggle through the laser source parameters on a user interface display menu. The action on the foot pedal assembly to toggle through the laser source parameters on the user interface display menu may include continuously depressing one foot actuator, and depressing and releasing at least one other foot actuator. Depressing and releasing one of the other foot actuators that is not continuously depressed may toggle forward through the laser source parameters to highlight one of the laser source parameters, and depressing and releasing the other of the other foot actuators that is not continuously depressed may toggle backward through the laser source parameters to highlight one of the laser source parameters. Releasing the continuously depressed foot actuator and depressing a different foot actuator may select the highlighted laser source parameter to be adjusted.

The first action or series of actions on the foot pedal assembly may include an action on the foot pedal assembly to increase or decrease a selected laser source parameter on a user interface display menu. The action on the foot pedal assembly to increase or decrease a selected laser source parameter may include continuously depressing one of the foot actuators, and depressing and releasing at least one of the other foot actuators that is not continuously depressed. Depressing and releasing one of the other foot actuators that is not continuously depressed may increase the selected laser source parameter, and depressing and releasing the other of the other foot actuators that is not continuously depressed may decrease the selected laser source parameter. The laser source may include at least two laser energy modes, and the method may further include adjusting a laser source parameter for each of the two laser energy modes. The second action or series of actions on the foot pedal assembly may include depressing and releasing only one of a plurality of pedals on the foot pedal assembly.

In another example, a laser energy system may include a laser energy source and an optical fiber coupled to the laser energy source, a control system having a plurality of adjustable settings for the laser energy source, and a foot pedal assembly, including at least three foot actuators. The three foot actuators may be selectively depressible to both adjust the plurality of adjustable settings and to activate the laser energy source.

The laser energy system may further include one or more of the following features. The laser energy source may include at least two laser modes and the control system may include a display unit, and each laser mode may include a plurality of adjustable parameters indicated on the display unit. The foot pedal assembly may further include a ready/standby actuator, and either depressing the ready/standby actuator or depressing one of the foot actuators may cause the control module to enter a laser parameter adjustment mode.

In another example, a medical system may include a laser energy source configured to be activated to produce and emit at least two laser modes, wherein the parameters of each of the two laser modes are selectively adjustable based on user input; a foot pedal assembly, wherein the foot pedal assembly is actuatable to selectively activate one of the two laser energies, and a medical device including a delivery shaft and at least one optical fiber, wherein the at least one optical fiber connects the laser energy source to a distal end of the delivery shaft.

The medical system may further include one or more of the following features. The foot pedal assembly may be actuatable to selectively adjust laser parameters for at least one of the two laser modes. The medical device may further include a deflection lever to deflect the distal end of the delivery shaft, and the laser energy source may further include a display unit to indicate a status of the at least two laser modes and to indicate at least a laser power, a laser energy, a frequency, and a pulse width for each of the two laser modes. The medical device may be configured for two hand use, and the foot pedal assembly may be configured be manipulated without input from a user's hands.

Both the foregoing general description and the following detailed description are exemplary and explanatory only and are not restrictive of the features, as claimed. As used herein, the terms "comprises," "comprising," "having," including," or other variations thereof, are intended to cover a non-exclusive inclusion such that a process, method, article, or apparatus that comprises a list of elements does not include only those elements, but may include other elements not expressly listed or inherent to such a process, method, article, or apparatus. Additionally, the term "exemplary" is used herein in the sense of "example," rather than "ideal." As used herein, the terms "about," "substantially," and "approximately," indicate a range of values within +/−5% of a stated value.

BRIEF DESCRIPTION OF THE FIGURES

The accompanying drawings, which are incorporated in and constitute a part of this specification, illustrate various exemplary embodiments and together with the description, serve to explain the principles of the disclosure.

FIGS. 3A-3C illustrate further examples of the medical system, according to aspects of the present disclosure.

DETAILED DESCRIPTION

Examples of the present disclosure include systems, devices, and methods to facilitate, and improve the efficacy, efficiency, and safety of laser energy delivery during medical procedures. For example, aspects of the present disclosure may provide a user (e.g., a physician, medical technician, or other medical service provider) with the ability to more easily adjust and set the parameters for the laser energy to be delivered within a patient. Some aspects of the present disclosure may be used in performing an endoscopic, hysteroscopic, or ureteroscopic procedure, such as, for example, a lithotripsy treatment, treating benign prostatic hyperplasia ("BPH"), or treating a cancerous tissue.

Reference will now be made in detail to examples of the present disclosure described above and illustrated in the accompanying drawings. Wherever possible, the same reference numbers will be used throughout the drawings to refer to the same or like parts.

The terms "proximal" and "distal" are used herein to refer to the relative positions of the components of an exemplary medical device or insertion device. When used herein, "proximal" refers to a position relatively closer to the exterior of the body or closer to an operator using the medical device or insertion device. In contrast, "distal" refers to a position relatively farther away from the operator using the medical device or insertion device, or closer to the interior of the body.

Figure 1:
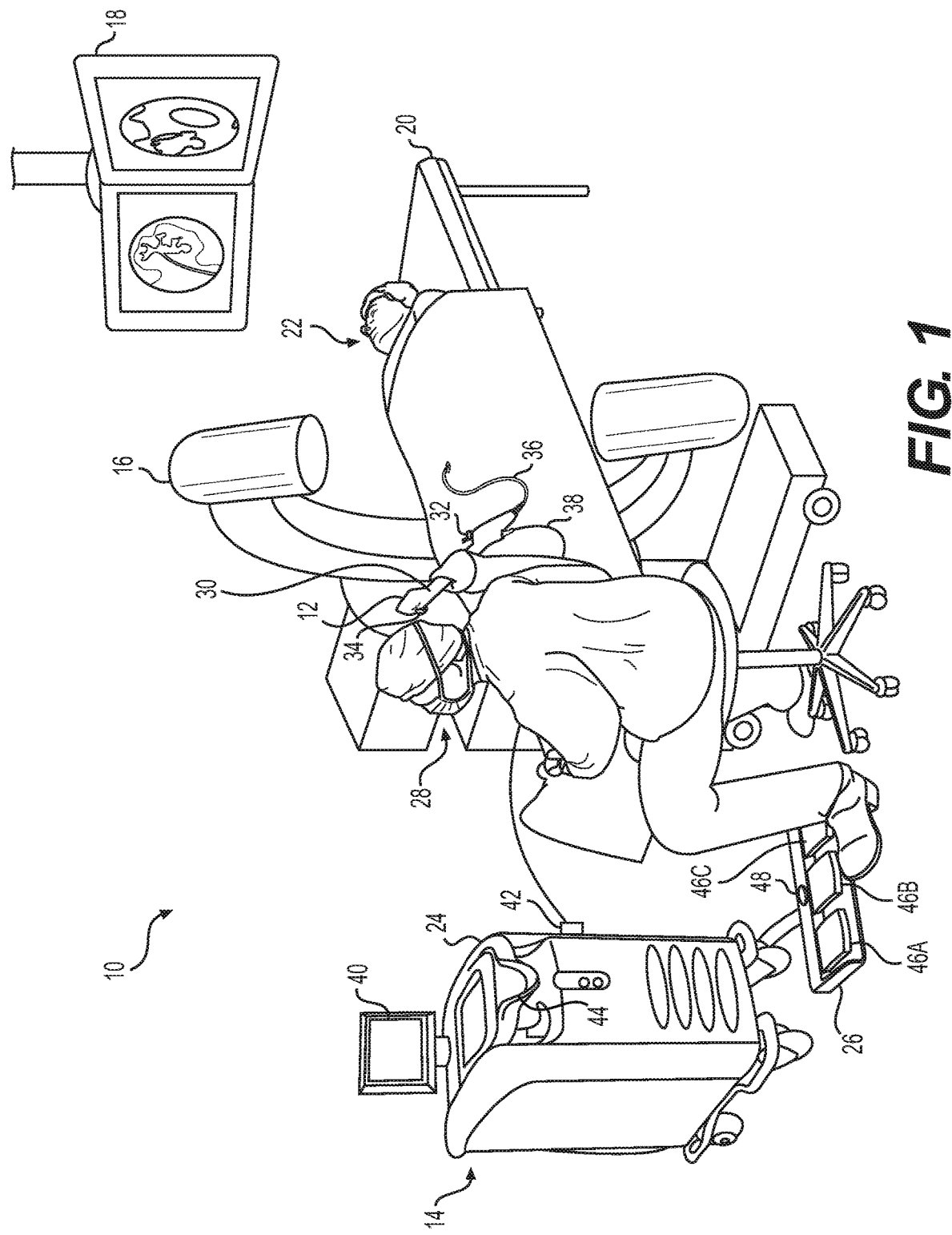
FIG. 1 illustrates a medical system, according to aspects of the present disclosure.

FIG. 1 illustrates a medical system 10 that includes a medical device 12 and an energy console 14. Medical system 10 may also include an imaging device 16, a display 18, and a patient support 20 for a patient 22. Medical device 12 may be wire connected (as shown), wirelessly connected, or otherwise coupled to energy console 14. Energy console 14 may include a laser control unit 24 and a user input, for example, a foot pedal assembly 26. Both medical device 12 and energy console 14 may be operated by a user 28.

Medical device 12 may be an insertion device such as, for example, a ureteroscope (e.g., LithoVue™ Single-Use Digital Flexible Ureteroscope by Boston Scientific Corp.). In another example, medical device 12 may be a cystoscope, and may include a plurality of lumens for optical fibers, fluid delivery or removal, imaging elements, etc. Medical device 12 may include a handle 30 with at least one port 32 and a deflection lever 34. Port 32 may be threaded and may include a T-connector as shown in FIG. 1, a Y-connector, or another appropriate connector. Medical device 12 may also include a delivery shaft 36 terminating distally in a distal end with at least one exit opening. The delivery shaft 36 may include a plurality of lumens, and the at least one port 32 may connect to a proximal end of the delivery shaft 36 through a lumen (not shown) in handle 30. A communication and power conduit 38 may connect laser control unit 24 to medical device 12. Both communication and power conduit 38 and an internal lumen in delivery shaft 36 may include optical fibers to deliver laser energy from laser control unit 24 to the distal end of delivery shaft 36. As such, laser control unit 24 and medical device 12 may be used to deliver laser energy to a lumen, tissue, or other material within patient 22. Alternatively, medical system 10 may include a laser fiber separate from communication and power conduit 38 that is connected to energy console 14, and the laser fiber may be delivered within the patient directly through a lumen in medical device 12, through a different insertion device, or through other known delivery methods.

Additional instruments or devices may be inserted through port 32 to be delivered to and/or out of the distal end of delivery shaft 36, such as, for example, a retrieval basket. The distal end of delivery shaft 36 may be manipulated by action on deflection lever 34. Handle 30 may also be connected to display 18 via an additional wired or wireless connection. For example, though not shown, medical device 12 may include an integral camera and/or a lighting element at the distal end of delivery shaft 36 that is/are connected to display 18. Alternatively, the integral camera and/or lighting element may transmit and receive signals to and from laser control unit 24 of energy console 14 via communication and power conduit 38. With medical device 12 positioned within patient 22, for example, through the patient's urethra to a patient's kidney, a retrieval device (not shown) may be inserted through port 32 and delivery shaft 36 and, using the integral camera and/or lighting element and deflection lever 34, a user may manipulate the distal end of delivery shaft 36 and extend the retrieval device to retrieve and remove material such as, for example, a kidney stone, with or without using laser lithotripsy by delivering laser energy from laser control unit 24 through the optical fiber in an additional lumen of medical device 12.

As mentioned above, energy console 14 includes laser control unit 24 and foot pedal assembly 26. Laser control unit 24 may include a user interface 40, which may be a liquid crystal display, a touch screen display, or other electronic display. As discussed in more detail below, user interface 40 may display a menu with a variety of adjustable laser parameters. Laser control unit 24 may also include a laser source port 42 such that a laser fiber within communication and power conduit 38 may couple laser control unit 24 to medical device 12 to deliver laser energy through an optical fiber in a lumen in delivery shaft 36 to the distal end of delivery shaft 36. As discussed, communication and power conduit 38 may be configured to transmit information from the camera at the distal end of the delivery shaft 36 to laser control unit 24 and/or display 18, and to also transmit laser energy through an optical fiber to be delivered to the distal end of delivery shaft 36. In another aspect, a separate laser fiber or cable may couple laser control unit 24 to medical device 12 and may transmit the laser energy through a fiber to be delivered to the distal end of delivery shaft 36. In a further aspect, medical device 12 may include a laser source within handle 30, and medical device 12 may include a wireless transceiver to wirelessly transmit signals to and receive signals from energy console 14. Laser control unit 24 may also include a medical device holder 44 such that medical device 12 may be securely positioned on or in laser control unit 24 when medical device 12 is not being used.

Foot pedal assembly 26 may include three individual actuators, for example, pedals 46A, 46B, and 46C. It is noted that foot pedal assembly 26 may include fewer than three pedals 46, for example, two, or may include greater than three pedals 46, for example, four or five. In one aspect, foot pedal assembly 26 may include a ready/standby actuator, for example, a ready/standby button 48. Ready/standby button 48 may allow a user to toggle between a "ready mode" where action on one of individual pedals 46A, 46B, and 46C may activate a laser source, and a "standby mode" where action on one of individual pedals 46A, 46B, and 46C would not activate the laser source. Alternatively, one of individual pedals 46A, 46B, and 46C may serve a ready/standby button 48. Furthermore, one pedal, e.g., 46A, may correspond to a first laser mode (e.g., a vaporization mode), and another pedal, e.g., 46C, may correspond to a second laser mode (e.g., a coagulation mode). The different laser modes may each include a set of parameters for a specific function. For instance, the parameters may include at least one of a laser power, a laser energy, a pulse width, a pulse frequency, and a pulse repetition frequency, etc. As such, foot pedal assembly 26 may allow a user to selectively activate one of a plurality of laser modes by selectively depressing one of pedals 46A, 46B, and 46C.

Although not shown, foot pedal assembly 26 may also include a protective screen, covering, or lock to protect pedals 46A, 46B, and 46C from accidental depression by a user, and thus ensure that laser control unit 24 is not accidentally activated. Furthermore, pedals 46A, 46B, and 46C may require a certain amount of pressure to be depressed to protect against inadvertent activation. Pedals 46A, 46B, and 46C may also include visual (e.g., different numbers, different colors, etc.) or tactile indications (e.g., different shapes, different ridge or texture patterns, etc.) such that the user may easily differentiate between pedals 46A, 46B, and 46C.

Foot pedal assembly 26 may be connected to laser control unit 24 via an adjustable wired connection such that foot pedal assembly 26 may be conveniently positioned for user 28 regardless of where laser control unit 24 is located. Alternatively, foot pedal assembly 26 may be wirelessly connected to laser control unit 24 via respective transceiver units.

Imaging device 16 may be any medical imaging device used to collect patient data. For example, imaging device 16 may include an X-ray, Magnetic Resonance Imaging, Computerized Tomography Scan, rotational angiography, ultrasound, or another appropriate internal imaging device. For some imaging procedures, a contrast agent may be used to assist in identifying anatomical features in the images. In one example, imaging device 16 is a mobile C-arm device useful for collecting X-ray images of patient 22 in preparation for and/or during a ureteroscopic procedure. Imaging device 16 may be coupled to energy console 14 and/or display 18, such that images obtained from imaging device 16 may be displayed on energy console 14 and/or display 18. For example, imaging device 16 may be used to collect patient images before a ureteroscopic procedure to locate and identify any stones or material to be removed. The user may consult the images for guidance on proper insertion and positioning of medical device 12, delivery shaft 36, and other instruments during the procedure. Imaging device 16 may also be used during a ureteroscopic procedure to collect images of the stones or material relative to an inserted ureteroscope within, for example, a patient's kidney. Imaging device 16 may also be used after a ureteroscopic procedure to determine whether all of the stones or material have been removed. In any of the aforementioned uses, imaging device 16 may be used in conjunction with the camera at the distal end of delivery shaft 36. For instance, a user may use imaging device 16 before a ureteroscopic procedure to locate the kidney stones and plan the procedure, and the user may user the camera at the distal end of delivery shaft 36 to visualize the stones and ensure that the laser energy will be directed at the stones.

Display 18 may be a single or dual screen display. In one example, one of the screens of display 18 may display an image or images currently or previously obtained by imaging device 16. The other screen may display an image or video obtained by the camera at the distal end of delivery shaft 36.

Patient support 20 may be a surgical stretcher, gurney, hospital bed, or surgical bed. Patient support 20 may be a urological surgical bed, and patient support 20 may allow imaging device 16 to capture images of patient 22 without interfering with imaging device 16.

Figure 2:
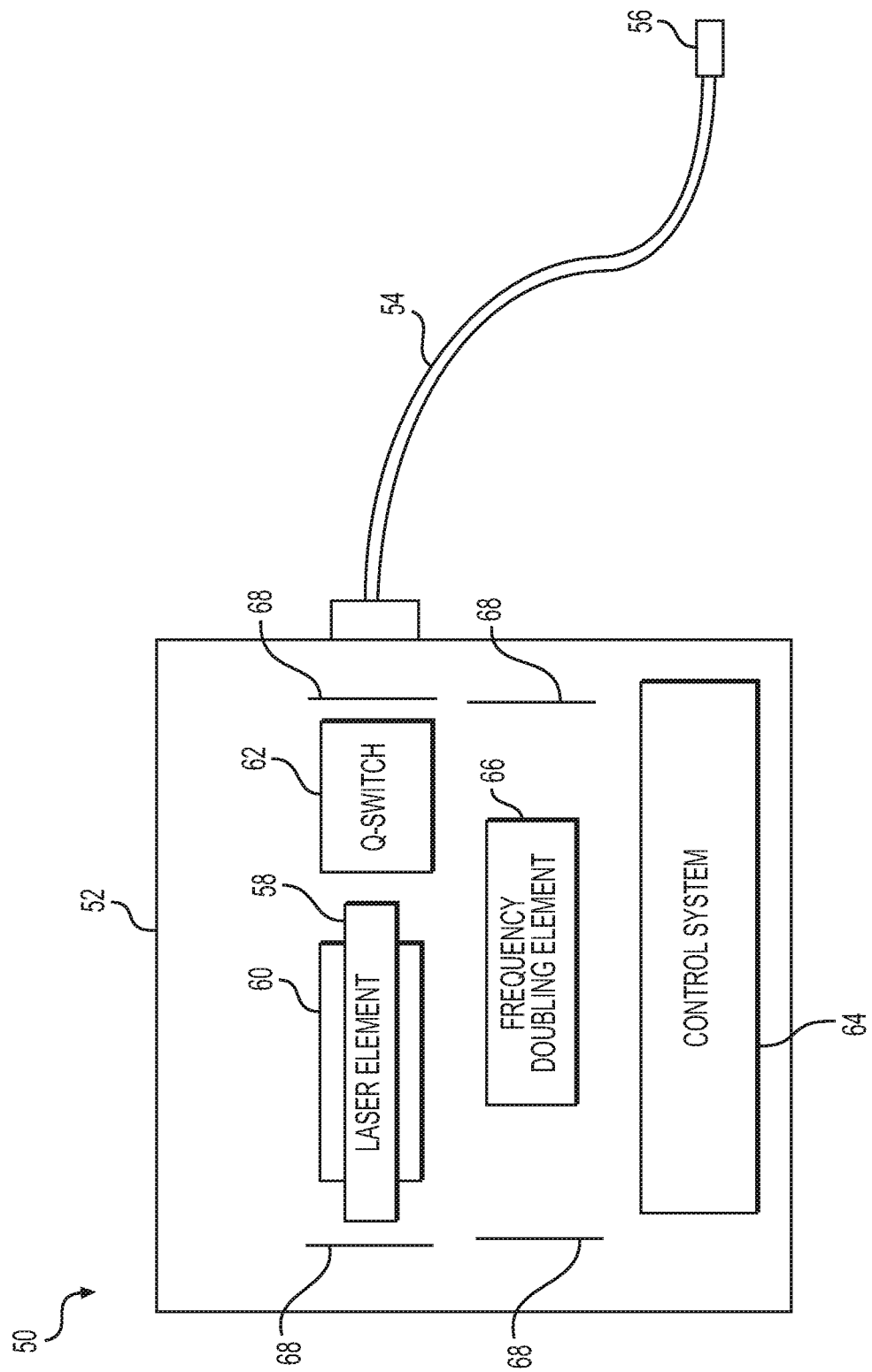
FIG. 2 illustrates an exemplary laser device, according to aspects of the present disclosure.

FIG. 2 illustrates an exemplary laser system 50, which may be internal to the laser control unit 24 of FIG. 1. As shown, laser system 50 includes a laser device 52, which may be a solid-state laser, to generate laser energy to be delivered through medical device 12. Laser system 50 may abut laser source port 42 of laser control unit 24, or may be coupled to laser source port 42 via an internal optical fiber. Laser system 50 may also include an optical fiber 54 with a tip 56 to be coupled to an internal optical fiber in medical device 12, for example, via communication and power conduit 38 being attached to laser source port 42. Alternatively, medical device 12 may include a separate optical fiber to be coupled to laser source port 42, or optical fiber 54 may otherwise be coupled to medical device 12 to deliver laser energy through delivery shaft 36.

Laser device 52 includes a laser element 58 and a pump source 60. Laser device 52 may also include a Q-switch 62, a control system 64, a frequency doubling element 66, and a series of mirrors 68. Control system 64 may be operably coupled to user interface 40 of laser control unit 24 and to foot pedal assembly 26. Laser element 58 may be a neodymium doped YAG (Nd:YAG) crystal, which emits light having a wavelength of 564 nm (infrared light) when excited by pump source 60. Laser element 58 may alternatively be fabricated from any suitable material (e.g., YAG, Lithium Yttrium Fluoride, Sapphire, Alexandrite, Spinel, Yttrium Orthoaluminate, Potassium Gadolinium Tungstate, Yttrium Orthovandate, or Lanthanum Scandium Borate). Laser element 58 is shown in a parallel relation with pump source 60, but it is noted that other geometries and configurations may be employed. Furthermore, it is noted that laser device 52 may emit pulsed laser energy or continuous wave laser energy. Additionally, the laser energy parameters that a user may set or adjust may depend on whether the laser energy is pulsed or continuous wave.

Optical fiber 54, whether within a lumen of medical device 12 or separate from medical device 12, may include cladding, shielding, jacketing and/or insulating layers. Optical fiber 54 may also include tip 56, and tip 56 may shape and/or orient laser energy emitted after passing through optical fiber 54. Additionally, although not shown, the distal end of delivery shaft 38 may include a distal tip of an optical fiber that may also shape and/or orient laser energy emitted from the distal end of delivery shaft 38. The shape and/or orientation of the laser energy may be modified based on the type of medical procedure. For example, treatments for BPH may include a side-firing distal tip at the distal end of delivery shaft 38, while laser lithotripsy for kidney stones may include a straight-firing distal tip.

Q-switch 62 may be operated in a repetitive mode to cause a train of micro-pulses to be generated by laser 52. The micro-pulses may be less than 1 microsecond in duration separated by about 40 microseconds, creating a quasi-continuous wave train. Q-switch 62 may be of the acousto-optic type, but may alternatively comprise a mechanical device such as a rotating prism or aperture, an electro-optical device, or a saturable absorber.

Control system 64 may control and operate laser device 52. For example, control system 64 may include a control processor which receives input from user 28 and processes the input to generate output signals to accordingly adjust the output of laser device 52. For example, user 28 may selectively adjust at least one of a laser energy, frequency, pulse width, wavelength, etc. via foot pedal assembly 26 of energy console 14, and control system 64 may control laser device 52 such that laser system 50 outputs laser energy having the adjusted parameters.

It is noted that frequency doubling element 66 is only exemplary. The generated laser energy may be internally or externally frequency doubled using non-linear crystals such as KTP, Lithium Triborate (LBO), or Beta Barium Borate (BBO) to produce second harmonic 532 nm green light, and higher harmonics. The frequency doubled, 532 nm wavelength, and the shorter wavelength higher harmonic beams may be more easily absorbed by tissue, promoting efficient tissue ablation.

Mirrors 68 may direct light from laser device 52 to frequency doubling element 66, and mirrors 68 may also form a resonant cavity within laser system 50. Mirrors 68 may be configured to focus the light to form an image just proximal to frequency doubling element 66. Mirrors 68 may also at least partially compensate for thermal lensing in laser system 50. Although mirrors 66 are illustrated as flat and parallel to the walls of laser system 50, the focusing may be achieved by curving and/or angling the mirrors. Alternatively, transmissive optical elements may be used to focus the light and compensate for thermal lensing. Other laser systems may be used, including but not limited to sapphire lasers, diode lasers, and dye lasers, which are adapted to provide the output power and wavelengths described herein, including wavelengths in the ranges from 70 nm to 500 nm and from 150 nm to 1800 nm. In one aspect, a greenlight laser system may be used, with a wavelength of approximately 532 nm. Here, laser element 58 may generate 1064 nm laser energy and, after frequency doubling by frequency doubling element 66, the output laser energy will have a wavelength of 532 nm. In another aspect, laser device 52 may generate laser energy having a wavelength of approximately 2100 nm (or 2.1 µm) in order to, for example, break a kidney stone.

Figure 3A:
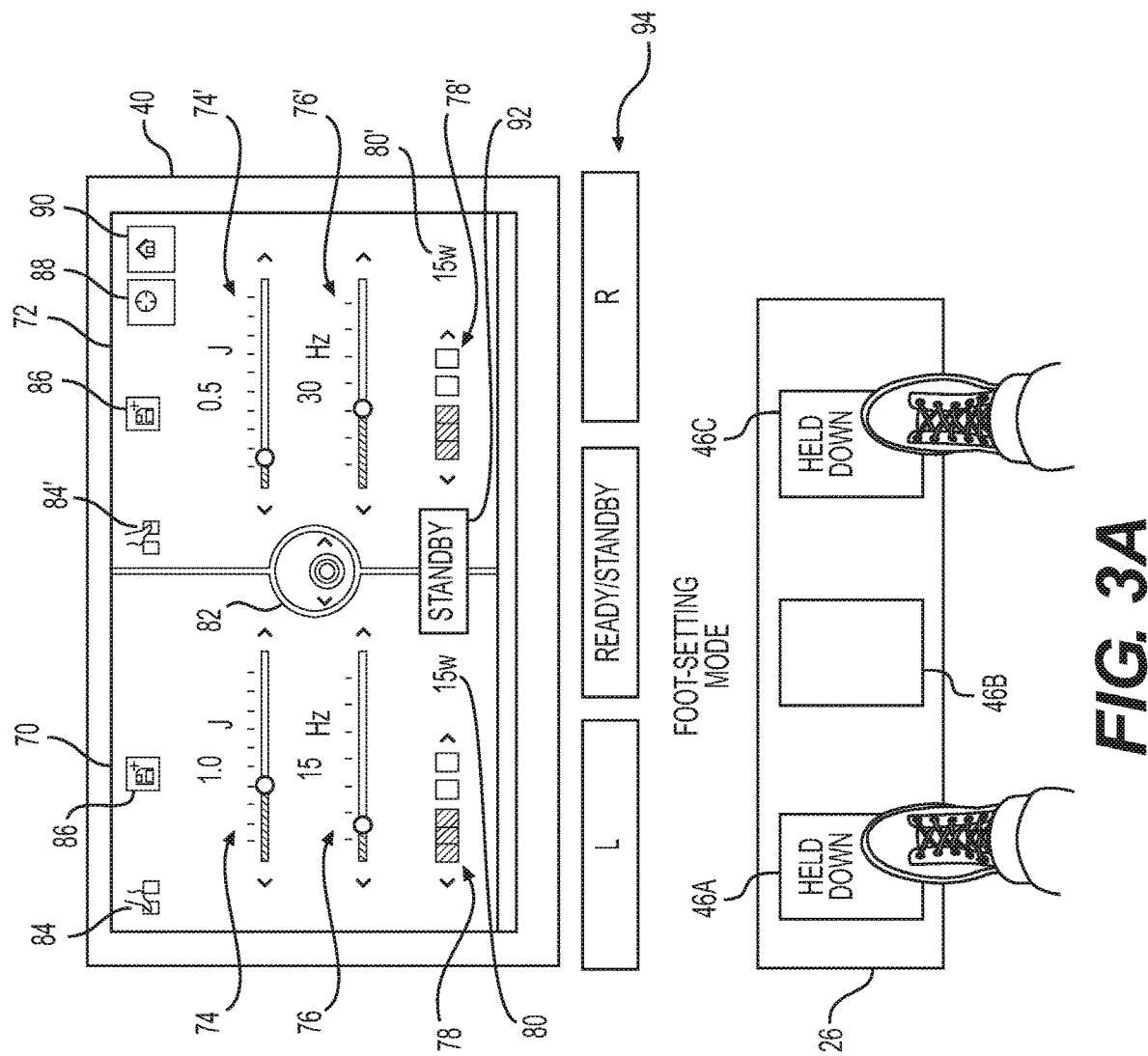
Figure 3B:
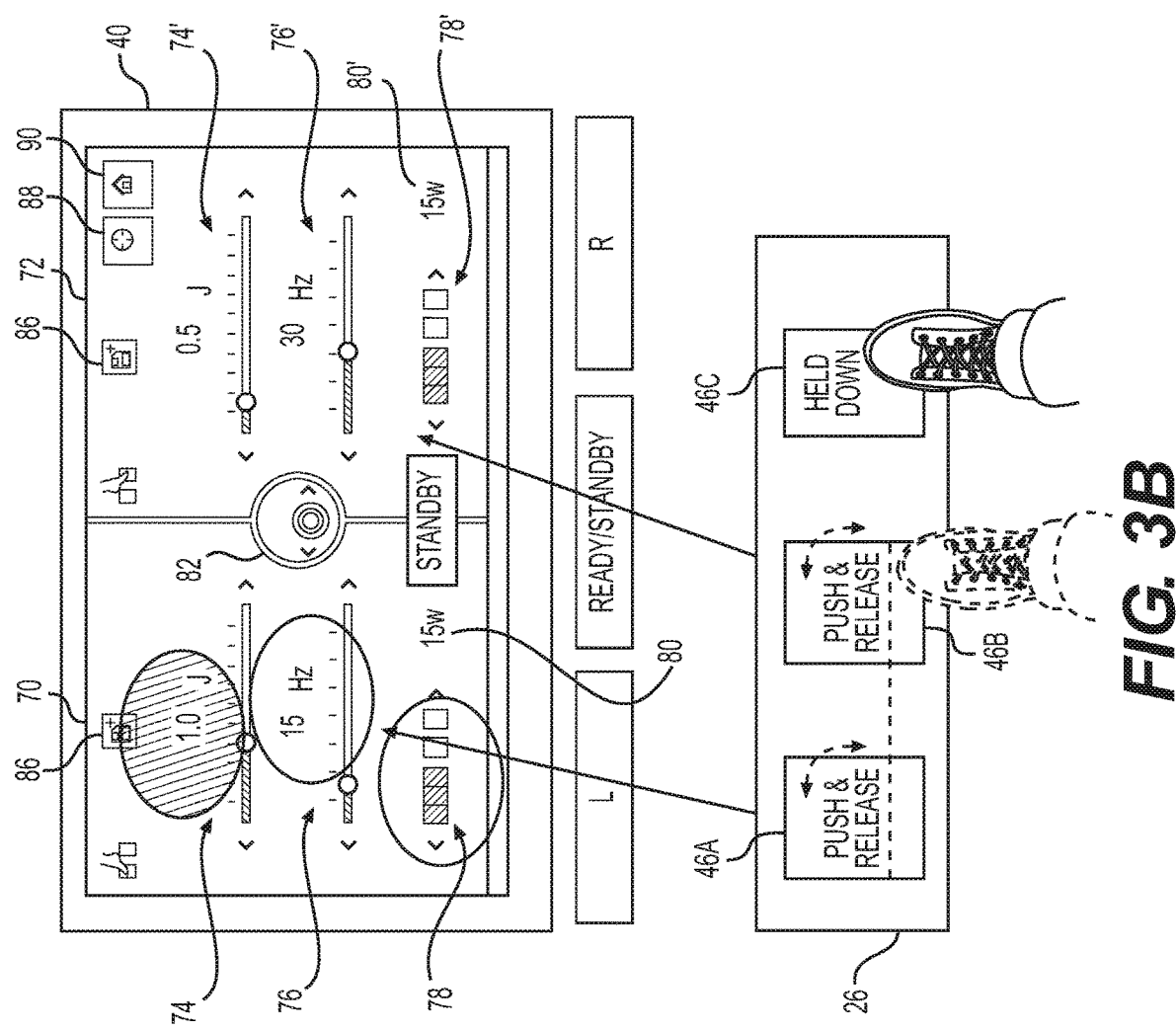

Turning now to FIGS. 3A-3C, the figures illustrate how a user may adjust and activate laser system 50 using foot pedal assembly 26. As shown in FIG. 3A, user interface 40 on laser control unit 24 may display a first laser mode 70 and a second laser mode 72. The two laser modes 70, 72 may vary depending on the procedure being performed, and each laser mode may vary based on laser energy 74, frequency 76, pulse width 78, etc. For example, for laser lithotripsy, first laser mode 70 may be for small kidney stones, while second laser mode 72 may be for larger kidney stones. In another aspect, for tissue removal, first laser mode 70 may be for tissue ablation, while second laser mode 72 may be for cauterization. As illustrated, first laser mode 70 may include different laser energy 74, frequency 76, and pulse width 78 than laser energy 74', frequency 76', and pulse width 78' of second laser mode 72. While both first laser mode 70 and second laser mode 72 are shown having the same wattage 80, 80', it is noted that first laser mode 70 and second laser mode 72 may include different wattages 80, 80'. It is also noted that the above laser parameters may be displayed via an incremental sliding scale, numerically, both, or in any other manner to convey the approximate value of the laser parameters to the user via user interface 40. Each of the aforementioned laser parameters may indicate both the currently set value and the range of values that user 28 may adjust each laser parameter within. Furthermore, user interface 40 may include an aiming beam brightness indicator 82, which a user may adjust to selectively adjust the brightness of an aiming beam. The aiming beam, or pilot beam, may indicate to a user the location to which the laser energy will be applied before the laser is activated, for example, through action on one of foot pedals 46A, 46B, or 46C.

As discussed above, the laser energy may include different adjustable parameters based on the type of laser energy. For example, if using pulsed laser energy, the user may set or adjust laser energy 74, frequency 76, and pulse width 78. If using continuous wave laser energy, the user need only set or adjust laser energy 74.

User interface 40 may also include other indicators. In one aspect, first laser mode 70 may include a foot pedal icon 84 indicating that first laser mode 70 corresponds to a left foot pedal, for example, pedal 46A, and second laser mode 72 may include a foot pedal icon 84' indicating that second laser mode 72 corresponds to a right foot pedal, for example, pedal 46C. Both first laser mode 70 and second laser mode 72 may include save icons 86, which may be selectable to save the adjusted settings. User interface 40 may also include a preset or default icon 88, which may allow a user to reset the settings to a preset or default setting. User interface 40 may include a home icon 90, which may allow a user to return to a home page different from the settings page. User interface 40 may also include a READY/STANDBY indicator 92, which may indicate whether laser control unit 24 is in a ready state, wherein the laser may be activated by action on foot pedal assembly 26, or whether laser control unit 24 is in a standby state, wherein the laser cannot be activated by action on foot pedal assembly 26. Furthermore, user interface 40 may include a foot pedal indication panel 94 to indicate, e.g., by illumination or shading, which foot pedal or foot pedals is/are currently depressed or otherwise activated.

In one aspect, and as discussed below in greater detail, action on foot pedal assembly 26 while laser control unit 24 is in a standby state may allow a user to modify the laser settings. As discussed above, foot pedal assembly 26 may include additional protections or locking devices to protect against accidental activation. It is also noted that user interface 40 may include additional information to be displayed to a user, such as, for example, a date and time, a duration of the procedure, a duration of total laser activation, a pulse count, a total energy delivered during the procedure, etc.

In one example, as shown in FIG. 3A, a user may hold down two foot pedals (e.g., foot pedals 46A and 46C), for a predetermined period of time to enter or exit the laser settings mode. Alternatively or additionally, a user may hold down a ready/standby switch or one foot pedal for a predetermined period of time to enter or exit the laser energy settings mode. As discussed above, foot pedal assembly 26 may include separate ready/standby switch 48 (FIG. 1), or one foot pedal 46 (e.g., foot pedal 46B) may correspond to the ready/standby switch.

FIG. 3B illustrates how a user may adjust the parameters for first laser mode 70 and second laser mode 72 through an action or a series of actions on foot pedal assembly 26. Once a user enters the laser setting mode as detailed with respect to FIG. 3A, a user may selectively toggle through the laser parameters on user interface 40. For example, a user may hold down foot pedal 46C and may tap, push and release, or otherwise manipulate one or both of foot pedals 46A and 46B to toggle through the laser parameters. The laser parameters and icons may be arranged in a particular order, such as, laser energy 74, then laser frequency 76, then pulse width 78, then wattage 80, then beam direction indicator 82, then save icon 86, etc. Pushing and releasing foot pedal 46B may toggle forward, while pushing and releasing foot pedal 46A may toggle backward between the parameters. User interface 40 may circle or otherwise highlight the selected parameter to indicate the selected parameter to the user. For example, FIG. 3B illustrates laser energy 74 for first laser mode 70 as being currently selected. Moreover, in some aspects, only one of first laser mode 70 and second laser mode 72 may be adjustable. Alternatively, a subset of the parameters displayed on user interface 40 may be locked or may only be adjustable within a specified range based on a previously entered information, such as, for example, the type of procedure being performed, the patient's age, etc.

In another aspect, pushing and releasing foot pedal 46A may toggle forward for first laser mode 70, and pushing and releasing foot pedal 46B may toggle forward for second laser mode 72. In this instance, the selected parameter may correspond to the most recently pushed and released foot pedal. For example, if a user pushes and releases foot pedal 46A a number of times to highlight frequency 76 for first laser mode 70 but then pushes and releases foot pedal 46B to highlight laser energy 74 for second laser mode 72, then laser energy 74 for second laser mode 72 may be the only selected parameter that the user may then adjust.

As shown in FIG. 3C, once the user has highlighted the parameter he or she wishes to adjust, he or she may adjust the position of his or her feet on foot pedal assembly 26. For example, a user may hold down foot pedal 46A to select a specific parameter to adjust that parameter. FIG. 3C illustrates that frequency 76' for second laser mode 72 is selected. Then, tapping, pushing and releasing, or otherwise manipulating foot pedals 46B and 46C may increase or decrease the set frequency 76'. For example, foot pedal 46B may correspond to an incremental decrease of frequency 76', and foot pedal 46C may correspond to an incremental increase of frequency 76'. The user may then exit that particular parameter by releasing the held down foot pedal, for example, by releasing held down foot pedal 46A.

The user may continue to toggle through the parameters and continue to adjust those parameters as discussed above with respect to FIG. 3B. The user may save the adjusted parameters using save icon 86. The user may also return the parameters to a default setting using default icon 88. The user may select to return to a home screen using home icon 90, for example, in order to view information about the patient or to view previously obtained images from a prior procedure or currently obtained from the camera at the distal end of delivery shaft 36. The home screen may also display a list of previously saved laser energy parameters, which the user may toggle through and select to be implemented and delivered within patient 22. Based on the information and/or images, the user may then return to the laser parameter display on user interface 40 and may adjust various parameters. Alternatively or additionally, the user may return to a ready mode by depressing and releasing one foot pedal or a combination of foot pedals, for example, foot pedal 46B, or by tapping ready/standby button 48 (shown in FIG. 1). Moreover, system 10 may return to a ready mode from the adjusting mode after a certain period of time.

Once system 10 is in the ready mode, the user may activate first laser mode 70 or second laser mode 72 to deliver laser energy with the adjusted parameters from the distal end of delivery shaft 36 through an action or series of actions on foot pedal assembly 26, for example, by selectively depressing one of foot pedals 46A, 46B, and 46C. Furthermore, the user may deactivate, turn off, or lock system 10 by depressing and releasing one foot pedal or a combination of foot pedals, for example, by depressing both foot pedal 46A and foot pedal 46B for a period of time. The user may then return to an active mode, turn on, or unlock system 10 by depressing and releasing one foot pedal or a combination of foot pedals, for example, by depressing both foot pedal 46B and foot pedal 46C for a period of time.

Although not shown, user interface 40 may include an icon and/or parameter related to display 18. For example, user interface 40 may include a display icon that allows a user to activate display 18 to display information about the patient or to view previously obtained images from a prior procedure or currently obtained from the camera at the distal end of delivery shaft 36. The information or images may be displayed on display 18 or on user interface 40. Furthermore, user interface 40 may include a parameter that may allow a user to zoom in or out and/or adjust the display settings of display 18. As such, a user may also adjust the information or images displayed on display 18 using foot pedal assembly 26.

While specific foot pedal combinations are discussed above, this disclosure is not so limited. In fact, different foot pedals or various combinations of foot pedals 46A, 46B, and 46C may be used to enter the parameter setting mode, to toggle through the parameters on user interface 40, to adjust the individual parameters, to return to a laser ready mode, and to activate the selected laser modes. Furthermore, as discussed above, more than three foot pedals may be used to perform the above procedures.

Figure 4:
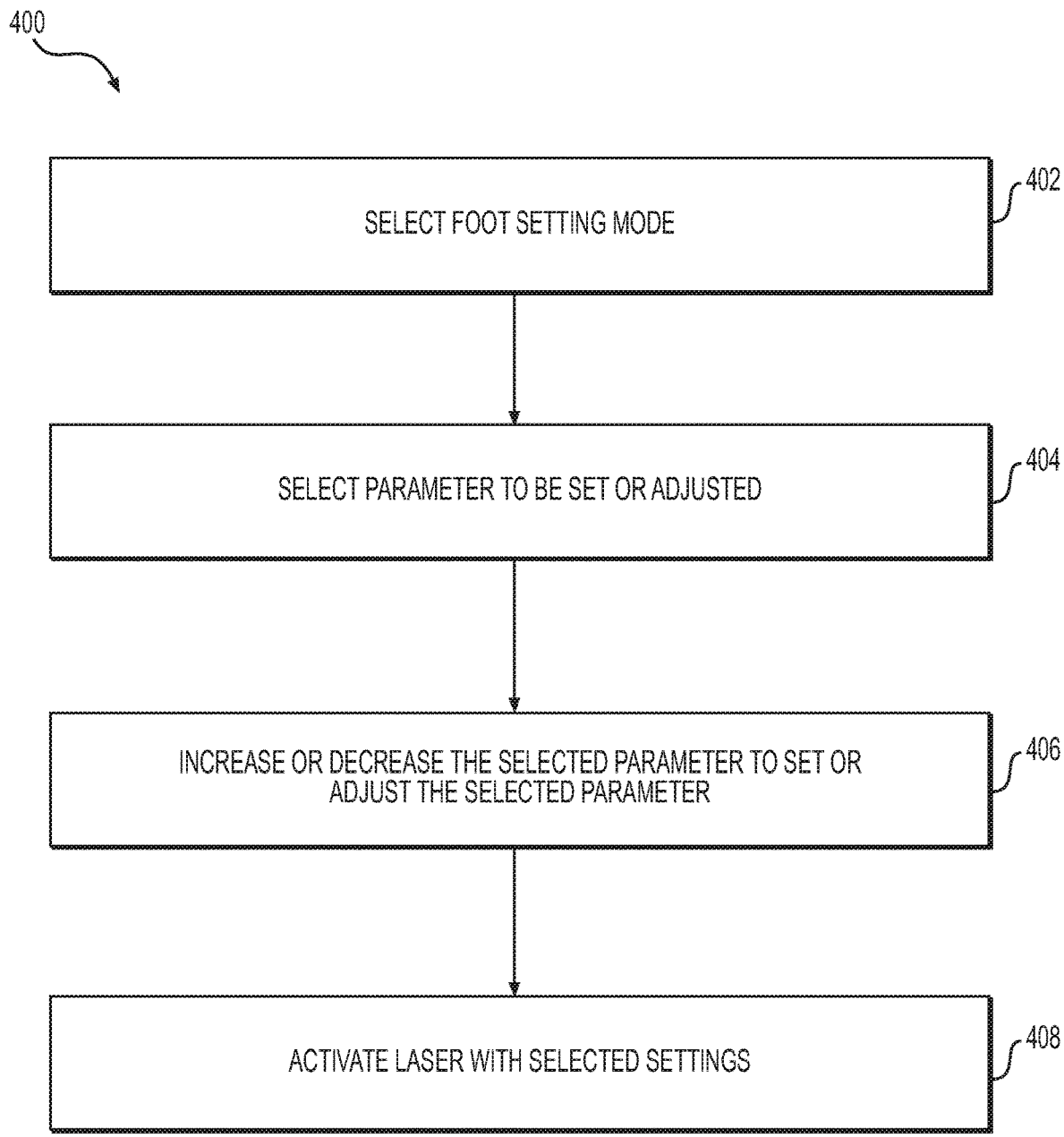
FIG. 4 is a flow diagram of an exemplary adjustment and setting method, according to aspects of the present disclosure.

FIG. 4 is a flow diagram portraying an exemplary adjustment and setting method 400 to adjust and set various parameters for at least one laser energy to be delivered in a medical procedure. Method 400 includes a step 402, wherein the user selects a foot setting mode. As discussed above, the user may select the foot setting mode by depressing one or more of foot pedals 46A, 46B, and 46C for a period of time. In a step 404, the user may select a parameter of the one or more laser energies to be set or adjusted. The user may toggle through the adjustable parameters by holding down one of foot pedals 46A, 46B, and 46C, and tapping, pushing and releasing, or otherwise manipulating one of the other foot pedals. The user may cycle through all of the parameters and icons on user interface 40, or based on pre-programmed settings, patient-specific details, or procedure-specific details, the user may cycle through a subset of the parameters and icons on user interface 40. In a step 406, the user may increase or decrease the selected parameter to adjust or set the selected parameter. Alternatively or additionally, step 406 may include selecting an icon displayed on user interface 40 to save or reset the selected parameters, or to modify the information displayed on user interface 40 or display 18.

In a step 408, the user may activate and deliver laser energy with the selected parameter settings. For example the user may tap, push and release, or otherwise manipulate one or more of foot pedals 46A, 46B, and 46C to exit the foot setting mode. The user may then tap, push and release, or otherwise manipulate one of foot pedals 46A, 46B, or 46C to activate laser device 52 with the parameter settings that correspond to the selected foot pedal. For instance, pushing and releasing foot pedal 46A may deliver laser energy of first laser mode 70, and pushing and releasing foot pedal 46C may deliver laser energy of second laser mode 72.

Although not shown, the user may repeat method 400 as many times as necessary to modify and deliver laser energy having a variety of parameters within patient 22. A user may also adjust the parameters during a medical procedure. For example, a user may deliver one or more laser energies within patient 22. Based on the progress and/or success of the procedure with the laser energies (e.g., observable via imaging device 16, display 18, and/or the camera at the distal end of delivery shaft 36), the user may enter the setting mode and adjust the parameters of the laser energies as discussed above. The user may then return to the laser ready mode and may deliver the adjusted laser energies to the patient.

While the above discussion is directed to two laser modes, the present disclosure is not so limited. For example, a foot pedal assembly 26 having three pedals 46 may include three laser modes. Alternatively or additionally, a different foot pedal assembly may include four pedals, which may correspond to four laser modes.

In the systems and methods discussed above, user 28 may adjust the parameters for laser energy to be delivered to treat tissue or material in a patient while also holding and maneuvering a medical device. For example, user 28 may adjust at least one of the power, the frequency, and the pulse width for the laser energy. User 28 may perform the above functions using only his or her feet and by applying selective pressure on foot pedal assembly 26. Moreover, the inputs on foot pedals 46 may vary from the inputs discussed above, and may be modified based on the user's dominant foot or other user preferences. User 28 may use his or her hands to control and/or position medical device 12, which may then be used to deliver laser energy through an optical fiber within a lumen of delivery shaft 36 or through an additional laser fiber delivered within the patient. As a result, user 28 need not let go of medical device 12, and user 28 need not be positioned within reach of laser control unit 24. For example, user 28 may easily and quickly position medical device 12, deliver laser energy through an optical fiber within a lumen to the distal end of delivery shaft 36, deflect the distal end of delivery shaft 36 using deflection lever 34, adjust various parameters of the laser energy, and then deliver the adjusted laser energy through the optical fiber to the deflected distal end of delivery shaft 36. The adjustments to the laser parameters may be made in the middle of a procedure without the need for assistance from additional medical professionals. Furthermore, user 28 may not need to sterilize laser control unit 24 as frequently since no one is not touching laser control unit 24 or user interface 40 during each procedure. Because user 28 may manipulate medical device 12 and adjust the laser parameters, the number of medical professionals and the duration of the medical procedure may also be reduced.

While principles of the present disclosure are described herein with reference to illustrative examples for particular applications, it should be understood that the disclosure is not limited thereto. Those having ordinary skill in the art and access to the teachings provided herein will recognize additional modifications, applications, embodiments, and substitution of equivalents all fall within the scope of the features described herein. Accordingly, the claimed features are not to be considered as limited by the foregoing description.

We claim:

1. A method of controlling a laser source to deliver laser energy through a medical device, comprising:

adjusting a laser source parameter including at least one of a laser power, a laser energy, a frequency, and a pulse width of the laser source, wherein the laser source parameters are adjustable through a first action or series of actions on a foot pedal assembly operably coupled to a laser control unit, wherein the foot pedal assembly includes a first foot actuator, a second foot actuator, and a third foot actuator; and activating the laser source, wherein the activation of the laser source includes a second action or series of actions on the foot pedal assembly, and wherein the second series of actions is different from the first series of actions, wherein the step of adjusting the laser source parameter includes:

an action on the foot pedal assembly to enter a laser settings mode by depression of only one foot actuator for a period of time or simultaneous depression of at least two foot actuators, and an action on the foot pedal assembly to toggle through the laser source parameters on a user interface display menu by continuously depressing one foot actuator and depressing and releasing at least one other foot actuator.

2. The method of claim 1, wherein the method further includes positioning the medical device by deflecting a distal end of a delivery shaft via action on a deflection lever on a handle of the medical device.

3. The method of claim 1, wherein the first action or series of actions on the foot pedal assembly includes simultaneous depression of at least two foot actuators to enter the laser settings mode.

4. The method of claim 1, wherein depressing and releasing one of the other foot actuators that is not continuously depressed toggles forward through the laser source parameters to highlight one of the laser source parameters, and wherein depressing and releasing the other of the other foot actuators that is not continuously depressed toggles backward through the laser source parameters to highlight one of the laser source parameters.

5. The method of claim 4, wherein releasing the continuously depressed foot actuator and depressing a different foot actuator selects the highlighted laser source parameter to be adjusted.

6. The method of claim 1, wherein another action or series of actions on the foot pedal assembly includes an action on the foot pedal assembly to increase or decrease a selected laser source parameter on the user interface display menu.

7. The method of claim 6, wherein the action on the foot pedal assembly to increase or decrease a selected laser source parameter includes continuously depressing one of the foot actuators, and depressing and releasing at least one of the other foot actuators that is not continuously depressed, and wherein depressing and releasing one of the other foot actuators that is not continuously depressed increases the selected laser source parameter, and wherein depressing and releasing the other of the other foot actuators that is not continuously depressed decreases the selected laser source parameter.

8. The method of claim 1, wherein the laser source includes at least two laser energy modes;

wherein the method further includes adjusting a laser source parameter for each of the two laser energy modes; and wherein the second action or series of actions on the foot pedal assembly includes depressing and releasing only one of a plurality of pedals on the foot pedal assembly.

9. A laser energy system comprising:

a laser energy source and an optical fiber coupled to the laser energy source;

a control system having a plurality of adjustable settings for the laser energy source;

a foot pedal assembly, including at least two foot actuators;

wherein the at least two foot actuators are selectively depressible to both adjust the plurality of adjustable settings and to activate the laser energy source, wherein the plurality of adjustable settings include at least one of a laser power, a laser energy, a frequency, and a pulse width of the laser energy source, wherein adjusting the plurality of adjustable settings for the laser energy source includes:

an action on the foot pedal assembly to enter a laser settings mode by depression of only one foot actuator for a period of time, and an action on the foot pedal assembly to toggle through the laser source parameters on a user interface display menu by continuously depressing one foot actuator and depressing and releasing at least one other foot actuator.

10. The laser energy system of claim 9, wherein the laser energy source includes at least two laser modes and the control system includes a display unit, and wherein each laser mode includes a plurality of adjustable parameters indicated on the display unit.

11. The laser energy system of claim 9, wherein the foot pedal assembly further includes a ready/standby actuator, and wherein either depressing the ready/standby actuator or depressing one of the foot actuators causes the control module to enter a laser parameter adjustment mode.

12. The laser energy system of claim 9, further comprising:

a medical device including a delivery shaft, wherein the optical fiber connects the laser energy source to a distal end of the delivery shaft, and wherein the medical device further includes a deflection lever to deflect the distal end of the delivery shaft.

13. The laser energy system of claim 9, wherein the laser energy source further includes a display unit to indicate a status of the one or more laser modes.

14. The laser energy system of claim 13, wherein the display unit indicates at least at least one of a laser power, a laser energy, a frequency, and a pulse width for each of the one or more laser modes.

15. The laser energy system of claim 12, wherein the medical device is configured for two hand use, and wherein the foot pedal assembly is configured to be manipulated without input from a user's hands.

16. A method of controlling a laser source to deliver laser energy through a medical device, comprising:

adjusting a laser source parameter including at least one of a laser power, a laser energy, a frequency, and a pulse width of the laser source, wherein the laser source parameters are adjustable through a first action or series of actions on a foot pedal assembly operably coupled to a laser control unit, wherein the foot pedal assembly includes a first foot actuator, a second foot actuator, and a third foot actuator; and activating the laser source, wherein the activation of the laser source includes a second action or series of actions on the foot pedal assembly, and wherein the second series of actions is different from the first series of actions, wherein the step of adjusting the laser source parameter includes:

an action on the foot pedal assembly to increase or decrease a selected laser source parameter on a user interface display menu by continuously depressing one of the foot actuators, and depressing and releasing at least one of the other foot actuators that is not continuously depressed, and wherein depressing and releasing one of the other foot actuators that is not continuously depressed increases the selected laser source parameter, and wherein depressing and releasing the other of the other foot actuators that is not continuously depressed decreases the selected laser source parameter.

17. The method of claim 16, wherein the laser source includes at least two laser energy modes.

18. The method of claim 17, wherein the method further includes adjusting a laser source parameter for each of the two laser energy modes.

19. The method of claim 18, wherein another action or series of actions on the foot pedal assembly includes depression of only one foot actuator for a period of time to enter a laser setting mode.

20. The method of claim 19, further including an action on the foot pedal assembly to toggle through the laser source parameters on a user interface display menu, wherein the action on the foot pedal assembly to toggle through the laser source parameters on the user interface display menu includes continuously depressing one foot actuator, and depressing and releasing at least one other foot actuator.

* * * * *